US011382586B2

United States Patent
Black

(10) Patent No.: US 11,382,586 B2
(45) Date of Patent: *Jul. 12, 2022

(54) PATIENT-SPECIFIC ANALYSIS OF RAW POSITRON EMISSION TOMOGRAPHY DATA

(71) Applicant: Richard R. Black, Russell, OH (US)

(72) Inventor: Richard R. Black, Russell, OH (US)

( * ) Notice: Subject to any disclaimer, the term of this patent is extended or adjusted under 35 U.S.C. 154(b) by 1133 days.

This patent is subject to a terminal disclaimer.

(21) Appl. No.: 14/826,511

(22) Filed: Aug. 14, 2015

(65) Prior Publication Data

US 2015/0342552 A1    Dec. 3, 2015

Related U.S. Application Data

(63) Continuation-in-part of application No. 14/495,991, filed on Sep. 25, 2014.

(Continued)

(51) Int. Cl.
*A61B 6/00* (2006.01)
*A61B 6/03* (2006.01)

(52) U.S. Cl.
CPC ............... *A61B 6/50* (2013.01); *A61B 6/037* (2013.01); *A61B 6/461* (2013.01); *A61B 6/469* (2013.01);

(Continued)

(58) Field of Classification Search
CPC ....... A61B 6/50; A61B 6/5217; A61B 6/5205; A61B 6/037; A61B 6/461; A61B 6/469;

(Continued)

(56) References Cited

U.S. PATENT DOCUMENTS

| 6,490,476 | B1 * | 12/2002 | Townsend | A61B 6/032 |
| | | | | 250/363.03 |
| 2003/0004405 | A1 * | 1/2003 | Townsend | A61B 6/032 |
| | | | | 600/407 |

(Continued)

FOREIGN PATENT DOCUMENTS

| KR | 20070082138 | 8/2007 |
| KR | 20130068817 | 6/2013 |

OTHER PUBLICATIONS

Adams, Michael C., et al. "A systematic review of the factors affecting accuracy of SUV measurements." American Journal of Roentgenology 195.2 (2010): 310-320.*

(Continued)

*Primary Examiner* — Sean D Mattson
(74) *Attorney, Agent, or Firm* — Tarolli, Sundheim, Covell & Tummino LLP

(57) ABSTRACT

Systems and methods are provided for evaluating tissue for abnormal glucose uptake within a region of interest within a patient. A PET scanner obtains PET imagery including the region of interest and at least part of the liver. An SUV calculator calculates a first set of SUVs representing the region of interest and a second set SUVs representing the liver from the set of at least one PET image. A standardization component calculates a correction value as a function of the second set of SUVs and applies the correction value to either a decision threshold associated with the region of interest or the first set of SUVs. A diagnosis component compares the first set of SUVs to the decision threshold to determine if the glucose uptake within the region of interest is abnormal. A display provides the determination to a user.

9 Claims, 3 Drawing Sheets

Related U.S. Application Data

(60) Provisional application No. 62/054,661, filed on Sep. 24, 2014, provisional application No. 61/984,246, filed on Apr. 25, 2014, provisional application No. 61/882,261, filed on Sep. 25, 2013.

(52) U.S. Cl.
CPC .......... *A61B 6/5205* (2013.01); *A61B 6/5217* (2013.01); *A61B 6/032* (2013.01)

(58) Field of Classification Search
CPC .. A61B 6/032; A61B 6/00; A61B 6/52; G16H 50/30
See application file for complete search history.

(56) References Cited

U.S. PATENT DOCUMENTS

| | | | |
|---|---|---|---|
| 2004/0030246 | A1 | 2/2004 | Townsend et al. |
| 2005/0215889 | A1* | 9/2005 | Patterson, II ............ G06K 9/00 600/436 |
| 2006/0018827 | A1 | 1/2006 | Dadachova et al. |
| 2007/0081712 | A1* | 4/2007 | Huang ...................... G06T 7/33 382/128 |
| 2008/0107229 | A1* | 5/2008 | Thomas .................. A61B 6/469 378/4 |
| 2010/0092051 | A1 | 4/2010 | Kadir et al. |
| 2010/0142775 | A1 | 6/2010 | Ganeshan et al. |
| 2011/0026797 | A1* | 2/2011 | Declerck ............... G06T 7/0012 382/131 |
| 2012/0123801 | A1* | 5/2012 | Opfer ..................... A61B 6/037 705/3 |
| 2012/0323108 | A1* | 12/2012 | Carroll .................. G06T 7/0014 600/407 |
| 2014/0126794 | A1* | 5/2014 | Ahn ...................... G06T 11/008 382/131 |
| 2014/0363063 | A1* | 12/2014 | Hendriks .............. G06T 7/0016 382/128 |

OTHER PUBLICATIONS

Paquet, Nancy, et al. "Within-patient variability of^ sup 18^ F-FDG: standardized uptake values in normal tissues." The Journal of Nuclear Medicine 45.5 (2004): 784.*
Shiono, Satoshi, et al. "Positron emission tomography for predicting recurrence in stage I lung adenocarcinoma: standardized uptake value corrected by mean liver standardized uptake value." European Journal of Cardio-Thoracic Surgery 40.5 (2011): 1165-1169.*
Boktor et al. (Boktor, Raef R., et al. "Reference range for intrapatient variability in blood-pool and liver SUV for 18F-FDG PET." Journal of Nuclear Medicine 54.5 (2013): 677-682. (Year: 2013).*
Soongsathitanon, Somphob, Pawitra Masa-Ah, and Malulee Tuntawiroon. "A new standard uptake values (SUV) calculation based on pixel intensity values." (2012). (Year: 2012).*
Bai, Bing, James Bading, and Peter S. Conti. "Tumor quantification in clinical positron emission tomography." Theranostics 3.10 (2013): 787. (Year: 2013).*
Wang, Yingbing, et al. "Standardized uptake value atlas: characterization of physiological 2-deoxy-2-[ 18 F] fluoro-d-glucose uptake in normal tissues." Molecular Imaging and Biology 9.2 (2007): 83-90. (Year: 2007).*
Paquet, Nancy, et al. "Within-patient variability of^ sup 18^ F-FDG: standardized uptake values in normal tissues." The Journal of Nuclear Medicine 45.5 (2004): 784.
Chinese Office Action for corresponding Chinese Application Serial No. 201480064488.2, dated May 17, 2018, pp. 1-7.
Hautzel et al., "Assessment of Large-Vessel Involvement in Giant Cell Arteritis with 18F-FDG PET: Introducing an ROC-Analysis-Based Cutoff Ratio", The Journal of Nuclear Medicine, vol. 49, No. 7, Jun. 13, 2008, pp. 1107-1113.

Shiono et al., "Positron Emission Tomography for Predicting Recurrence in Stage 1 Lung Adenocarcinoma: Standardized Uptake Value Corrected by Mean Liver Standardized Uptake Value", European Journal of Cardio-Thoracic Surgery, Springer Verlag, Berlin DE, vol. 40, No. 5, Feb. 4, 2011, pp. 1165-1169.
Extended European Search Report dated Apr. 18, 2017 for corresponding European Application No. 14850017.6.
Bagheri et al., "Characterization of the Normal Adrenal Gland with F-FDG PET/CT" The Journal of Nuclear Medicine, vol. 45, No. 8, Aug. 2004, p. 1340.
Turkington et al., "Clinical Oncologic Positron Emisson Tomography: An Introduction" Seminars in Roentgenology, vol. 37, No. 2, Apr. 2002, p. 102.
Gupta et al., "Clinical Role of F-18 Fluorodeoxyglucose Positron Emission Tomography Imaging in Patients with Lung Cancer and Suspected Malignant Pleural Effusion" www.chestjournal.org, Chest, vol. 22, No. 6, Dec. 2002, p. 1919.
Tylksi et al., "Comaprative Assessment of Methods for Estimating Tumor Volume and Standardized Uptake Value in F-FDG PET" The Journal of Nuclear Medicine, vol. 51, No. 2, Feb. 2010, p. 268.
Skougaard, et al., "Comparison of EORTC Criteria and PERCIST for PET/CT Response Evaluation of Patients with Metastatic Colorectal Cancer Treated with Irinotecan and Cetuximab" The Journal of Nuclear Medicine, vol. 54, No. 7, Jul. 2013, p. 1026.
Wade, "Derivation Versus Validation" Arch. Dis. Child., vol. 83, 2000, p. 459.
Thie et al., "The Diagnostic Utility of the Lognormal Behavior of PET Standardized Uptake Values in Tumors" The Journal of Nuclear Medicine, vol. 41, No. 10, Oct. 2000, p. 1664.
Delbeke et al., "Evaluation of Benigh vs Malignant Hepatic Lesions with Positron Emissin Tomography" American Medical Associates, Arch. Surg., vol. 133, May 1998, p. 510.
Gonzalez et al., "F18-FDG Heart Uptake in Oncologic Pet Studies" www.alasbimnjournal.cl/revistas/11/gonzaleztotal.html, downloaded Oct. 2, 2014.
Boellaard et al., "FDG PET and PET/CT: EANM Procedure Guidelines for Tumour PET imaging: Version 1.0" Eur. J. Nucl. Med. Mol. Imaging, vol. 37, 2010, p. 181.
Ramos et al. "FDG-PET Standardized Uptake Values in Normal Anatomical Structures Using Iterative Reconstruction Segmented Attenuation Correction and Filtered Back-Projection" European Journal of Nuclear Medicine, vol. 28, No. 2, Feb. 2001, p. 155.
Wahl et al., "From RECIST to PERCIST: Evolving Considerations for PET Response Criteria in Solid Tumors" The Journal of Nuclear Medicine, vol. 50, No. 5, May 2009, p. 112S.
Bustamante et al., "High Aerobic Glycolysis of Rat Hepatoma Cells in Culture: Role of Mitochondrial Hexokinase" Proc. Natl. Acad. Sci., vol. 74, No. 9, Sep. 1977, p. 3735.
Tomasi et al., "Importance of Quantification for the Analysis of PET Data in Oncology: Review of Current Methods and Trends for the Future" World Molecular Imaging Society, vol. 14, 2012, p. 131.
Itti, et al., "Improvement of Early F-FDG PET Interpertation of Diffuse Large B-Cell Lymphoma: Importance of the Reference Background" The Journal of Nuclear Medicine, vol. 51, 2010, p. 1857.
Laffon et al., "Is liver SUV Stable Over Tme in F-FDG PET Imaging" J. Nucl. Med. Technol., vol. 39, 2011, p. 258.
Patel et al., "The Lace of Evidence for PET or PET/CT Surveillance of Patients with Treated Lymphoma, Colorectal Cancer, and Head and Neck Cancer: A Systematic Review" The Journal of Nuclear Medicine, vol. 54, No. 9, Sep. 2013, p. 1518.
Vansteenkiste et al., "Lymph Node Staging in Non-Small-Cell Lung Cancer with FDG-PET Scan: A Prospective Study on 690 Lymph Node Stations from 68 Patients" Journal of Clinical Oncology, vol. 16, No. 6, Jun. 1998, p. 2142.
Black, "Standarized Quantitative Analysis-Interperation of FDG PET-CT in Adrenal Gland and Pleural Based Malignancy" manuscript, 33 pages.
Young et al., "Measurement of Clinical and Subclinical Tumour Response using [ 18F]-Fluorodeoxyglucose and Positron Emission Tomography: Review and 1999 EORTC Recommendations" European Journal of Cancer, vol. 35, No. 1, 1999, p. 1773.

(56) References Cited

OTHER PUBLICATIONS

Geworski, et al., "Multicenter Comparison of Calibration and Cross Calibration of PET Scanners" The Journal of Nuclear Medicine, Vo. 43, No. 5, May 2002, p. 635.

Kuruva, et al., "Multivariate Analysis of Various Factors Affecting Background Liver and Mediastinal Standardized Uptake Values" Indian Journal of Nuclear Medicine, vol. 27, Issue 1, Jan.-Mar. 2012, p. 20.

Boellared "Need for Standardization of 18F-FDG PET/CT for Treatment Response Assessments" The Journal of Nuclear Medicine, vol. 52, Dec. 2011, p. 93S.

Warburg, "On the Origin of Cancer Cells" Science, vol. 123, No. 3191, Feb. 24, 1956, p. 309.

Kinahan et al. "Poistron Emission Tomography-Computed Tomography Standardized Uptake Values in Clinical Practice and Assessing Response to Therapy" Elsevier, 2310, p. 496.

Delbeke et al., "Procedure Guideline for Tumor Imaging with 18F-FDG PET/CT 1.0" 2006, 11 pages.

Lowe et al., "Prospective Investigation of Positron Emission Tomography in Lung Nodules" Journal of Clinical Oncology, vol. 16, No. 3, Mar. 1998, p. 1075.

Scheuermann et al., "Qualifiation of PET Scanners for Use in Multicenter Cancer Clinical Trails: The American College of Radiology Imaging Network Experience" J. Nucl. Med., vol. 50, 2009, p. 1187.

Bunyaviroch et al., "Quantitative Effects of Contrast Enhanced CT Attenuation Correction of PET SUV Measurements" Mol. Imaging Biol., vol. 10, 2008, p. 107.

Boktor, et al., "Reference Range for Intrapatient Variability in Blood-Pool and Liver SUV for 18F-FDG PET" J. Nucl. Med. vol. 54, 2013, p. 677.

Fletcher, et al., "Recommendations on tee Use of 18F-FDG PET in Oncology" The Journal of Nuclear Medicine, vol. 49, No. 3, Mar. 2008, p. 480.

Hillner et al., "Relationship Between Cancer Type and Impact of PET and PET/CT on Intended Management: Findings of the National Oncologic PET Registry" The Journal of Nuclear Medicine, vol. 49, No. 12, Dec. 2008, p. 1928.

Keyes, Jr., "Suv: Standard Uptake or Silly Useless Value?" The Journal of Nuclear Medicine, vol. 36, No. 10, Oct. 1995, p. 1836.

Boellard, "Standards for PET Image Acquisition and Quantitative Data Analysis" J. Nucl. Med., vol. 50, 2009, p. 11S.

Adams et al., "A Systematic Review of the Factors Affecting Accuracy of SUV Measurements" AJR, vol. 195, Aug. 2010, p. 310.

Otsuka et al., "The Effect of Oral Contrast on large Bowel Activity in FDG-PET/CT" Annals of Nuclear Medicine, vol. k 19, No. 2, 2005, p. 101.

Boellaard et al., "The Netherlands Protocol for Standardisation and Quantification of FDG Whole Body PET Studies In Multi-Centre Trials" Eur. J. Nucl. Med. Mol. Imaging, vol. 35, 2008, p. 2320.

Benz et al., "Treatment Monitoring by 18F-FDG PET/CT in Patients with Sarcomas: Interobserver Variability of Quantitative Parameters in Treatment-Induced Changes in Histophathologically Responding and Nonresponding Tumors" The Journal of Nuclear Medicine, vol. 49, No. 7, Jul. 2008, p. 1038.

Kanstrup et al., "Variability and Reproducibility of Hepatic FDG Uptake Measured as SUV as well as Tissue-to-Blood Background Ratio using Positron Emission Tomography in Healthy Humans" Scandinavian Society of Clinical Physiology and Nuclear Medicine, vol. 29, No. 2, 2008, p. 108.

Graham et al., "Variations in PET/CT Methodology for Oncologic Imaging at U.S. Academic Medical Centers: An Imaging Response Assessment Team Survey" J. Nucl. Med., vol. 52, 2011, p. 311.

"Cancar Fact Sheet No. 297" WHO Cancer, updated Feb. 2014, www.who.int/mediacentre/factsheets/fs297/en/.

Paquet et al., "Within-Patient Variability of 18F-FDG: Standardized Uptake Values in Normal Tissues" The Journal of Nuclear Medicins, vol. 45, No. 5, May 2004, p. 784.

* cited by examiner

PATIENT-SPECIFIC ANALYSIS OF RAW POSITRON EMISSION TOMOGRAPHY DATA

RELATED APPLICATIONS

This application is a continuation-in-part of and claims priority to U.S. patent application Ser. No. 14/495,991, filed Sep. 25, 2014, which, in turn, claims priority to each of U.S. Provisional Patent Application Ser. No. 62/054,661 filed Sep. 24, 2014, U.S. Provisional Patent Application Ser. No. 61/984,246 filed Apr. 25, 2014, and U.S. Provisional Patent Application Ser. No. 61/882,261 filed Sep. 25, 2013. Each of these applications is hereby incorporated by reference.

BACKGROUND OF THE INVENTION

Field of the Invention

The invention relates generally to medical imaging. More specifically, the invention relates to patient-specific analysis of positron emission tomography data.

Background of the Invention

The early diagnosis, appropriate staging, and the subsequent assessment of treatment outcomes of various malignancies can be enhanced by modern imaging techniques. In 1956, Warburg suggested that many malignant cells utilize anaerobic consumption of glucosepyruvate, as the primary energy source. Two decades later, Bustamonte et al proposed using radiolabeled glucose for cancer detection since glucose metabolism in malignant cells may exceed two hundred times the glycolytic rates of normal non-neoplastic cells. Consequently, the application of these findings has expanded significantly by using radiolabeled 18F deoxyglucose (FDG) positron emission tomography (PET) for physiologic imaging of malignancies, often combined with computed tomographic (CT) imaging for anatomic detail.

The key to correct interpretation of the 18 FDG PET-CT image data sets is to be able consistently to differentiate between normal uptake, abnormal-nonmalignant uptake, and abnormal-malignant uptake of the radiopharmaceutical. One way this can be accomplished is by visual comparison of uptake in the target lesion with that in the mediastinal blood pool or liver parenchyma. Such a qualitative approach is subjective and may be associated with poor reproducibility. Readily applicable, less subjective evaluations may be possible with 18 FDG PET using count statistics that reflect uptake of 18 FDG. The Standard Uptake Value (SUV) for potentially differentiating malignant and non-malignant disease is one such application. The SUV is an actual measurement of the amount of 18 FDG within a region of interest corrected for the administered dosage of FDG, time of injection, and the patient's body weight.

SUMMARY OF THE INVENTION

In accordance with an aspect of the present invention, a system is provided for evaluating tissue for abnormal glucose uptake within a region of interest within a patient. The system includes a positron emission tomography (PET) scanner configured to obtain a set of at least one PET image that includes a first set of at least one intensity value representing the region of interest and a second set of at least one intensity value representing a liver of the patient. A standardization component is configured to calculate a correction value as a function of the second set of at least one intensity value and apply the correction value to a chosen one of a decision threshold associated with the region of interest and the first set of at least one intensity value. A diagnosis component is configured to compare the first set of intensity values to the decision threshold associated with the region of interest to determine if the glucose uptake within the region of interest is abnormal. A display is configured to display the determination if the glucose uptake within the region of interest is abnormal to a user.

In accordance with another aspect of the present invention, a method is provided for evaluating tissue for abnormal glucose uptake within a region of interest within a patient. A positron emission tomography (PET) scan is performed at an associated PET scanner to provide a first set of at least one intensity value representing the region of interest and a second set of at least one intensity value representing a liver of the patient. A correction value is calculated as a function of the second set of at least one intensity value. The correction value is applied to a chosen one of a decision threshold associated with the region of interest and the first set of at least one intensity value. The first set of at least one intensity value is compared to the decision threshold associated with the region of interest.

In accordance with yet another aspect of the present invention, a system includes an operatively connected set of at least one non-transitory computer readable medium. Each non-transitory medium is operatively connected to at least one associated processor and stores machine executable instructions. The instructions are executable by the at least one associated processor to evaluate tissue for abnormal glucose uptake within a region of interest within a patient. The machine executable instructions include a client interface configured to receive a first set of at least one intensity value representing the region of interest and a second set of at least one intensity value from the hepatic parenchyma. A standardization component is configured to calculate a correction value as a function of the second set of at least one intensity value and apply the correction value to a chosen one of a decision threshold associated with the region of interest and the first set of at least one intensity value. A diagnosis component is configured to compare the first set of at least one intensity value to the decision threshold associated with the region of interest to determine if the glucose uptake within the region of interest is abnormal. The client interface is configured to provide the determination if the glucose uptake within the region of interest is abnormal to an associated client device.

BRIEF DESCRIPTION OF THE DRAWINGS

The features, objects, and advantages of the invention will become more apparent from the detailed description set forth below when taken in conjunction with the drawings, wherein.

DETAILED DESCRIPTION OF THE INVENTION

One widely used SUV threshold for the categorization of neoplastic versus non-neoplastic disease is considered to be 2.5. It has been suggested, however, that different thresholds for the designation of malignant disease based on the location of involvement, so that the commonly utilized value of 2.5 may be associated with an overall decrease in specificity. To further complicate the use of the SUV in the evaluation of individuals with suspected malignant disease, variability in the SUVs between and within individuals may occur on the same imaging device. The use of serial examinations on file same patient using different devices further increases the inconsistency and reduces the overall accuracy of the individual examination.

In accordance with an aspect of the present invention, systems and methods are provided for patient-specific analysis of positron emission tomography (PET) images. Specifically, the inventor has determined that the stability of glucose uptake in the liver can be exploited to provide a patient-specific correction to a measured raw PET value in an arbitrary location within the body. It will be appreciated that since the measured intensity value is useful mainly relative to one or more associated decision thresholds for distinguishing between diseased (e.g., cancerous) and healthy tissue, and thus it is generally functional equivalent, the correction value can either be applied to the measured intensity values or an inverse of the correction factor can be applied to the decision thresholds.

Figure 1:
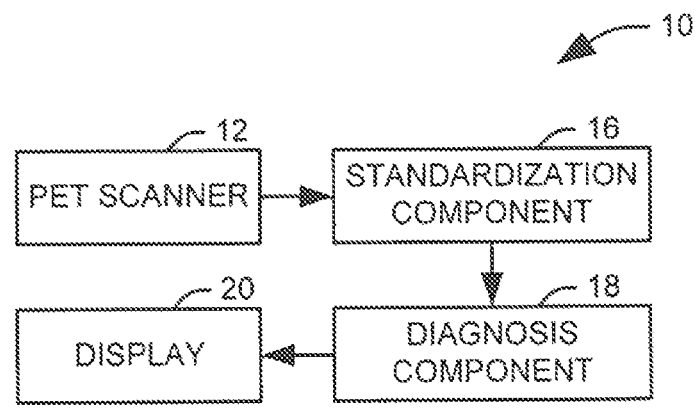
FIG. 1 illustrates a system for evaluating tissue for abnormal glucose uptake within a region of interest within a patient in accordance with an aspect of the present invention.

FIG. 1 illustrates a system 10 for evaluating tissue for abnormal glucose uptake within a region of interest within a patient in accordance with an aspect of the present invention. The system 10 includes a positron emission tomography (PET) scanner 12 configured to obtain a set of at least one PET image that includes the region of interest and at least a portion of a liver of the patient. In one implementation, the PET scanner is a positron emission tomography/computed tomography (PET-CT) scanner configured to provide PET and CT data tor the region of interest and the liver. From these images, a first set of at least one intensity value, representing the region of interest, and a second set of at least one intensity value, representing the liver, can be determined.

A standardization component 16 is configured to calculate a correction value as a function of the second set of intensity values and apply the correction value to a chosen one of a decision threshold associated with the region of interest and the first set of intensity values. In one implementation, the standardization component is configured to calculate a ratio including a value representing the second set of intensity values and an average liver SUV for a population of patients. In one implementation, the average value for a population of patients is in a range between 1.5 and 3, and in another implementation, a value substantially equal to 2.0 can be used. It will be appreciated that functions other than this ratio can be used to calculate the correction factor as well as variations on this ratio. For example, the correction value can be calculated as a product of the ratio and a scaling factor and/or sum of the ratio and an offset value.

The inventor has found the liver tissue, particularly the hepatic parenchyma, has a relatively stable glucose uptake over time, allowing it to be used to standardize the measured intensity values to account for differences among patient physiologies. In one implementation, an intensity for each of a plurality of regions within the hepatic parenchyma and a mean value is calculated across the plurality of regions to provide an intensity value representing the liver for the correction value. In one implementation, the population of patients used to determine the average liver SUV is a proper subset of all patients for whom measured SUVs of the liver are available, selected according to at least one biometric parameter with the patient. For example, the average liver SUV tor the population can be measured for patients sharing one or more of a sex, an age cohort, or a particular disorder with the patient.

Once the correction value has been calculated, it is provided to a diagnosis component 18 configured to compare the first set of SUVs to the decision threshold associated with the region of interest to determine if the glucose uptake within the region of interest is abnormal. In one implementation, the decision threshold is selected based on previously acquired data for a particular location within the body and type of tissue. In another implementation, the diagnosis component 18 calculates the decision threshold associated with the region of interest as a function of a previously measured SUV that has been corrected by a previously calculated correction factor. In general, this might be done to track disease progression or treatment efficacy. A display 20 is configured to display the determination if the glucose uptake within the region of interest is abnormal to a user.

For the implementation in which the correction value is calculated as a ratio, the condition for which a patient will be found to have abnormal glucose uptake in the region of interest can be expressed as:

$$\frac{a \mu_{SUV}}{l} > T \qquad \text{Eq. 1}$$

where a is a value representing the measured activity values within the region of interest, such as an average value or a measured activity value, l is a value representing the measured activity values within the liver, $\mu_{SUV}$ is an average SUV for a population of interest, and T the decision threshold. It will be appreciated that both $\mu_{SUV}$ and l will be positive values and thus it does not matter if the correction value is applied to the measured value, a, or if the multiplicative inverse of the correction value is applied to the threshold value, T, for our purposes.

An SUV value calculated for a given patient can be represented in general terms as xA(t), in which x is an activity value measured at time t, and A(t) is a combination of factors specific to the patient and the PET agent used, such as body weight and the injected activity. Assuming that the measurements of the first set of intensity values and the second set of intensity values can be performed simultaneously or over a short period of time, the value for A(t) for both measurements will be substantially the same. Accordingly, the decision threshold, T, can be taken from current SUV thresholds, as the resulting corrected value is effectively a corrected SUV value.

Figure 2:
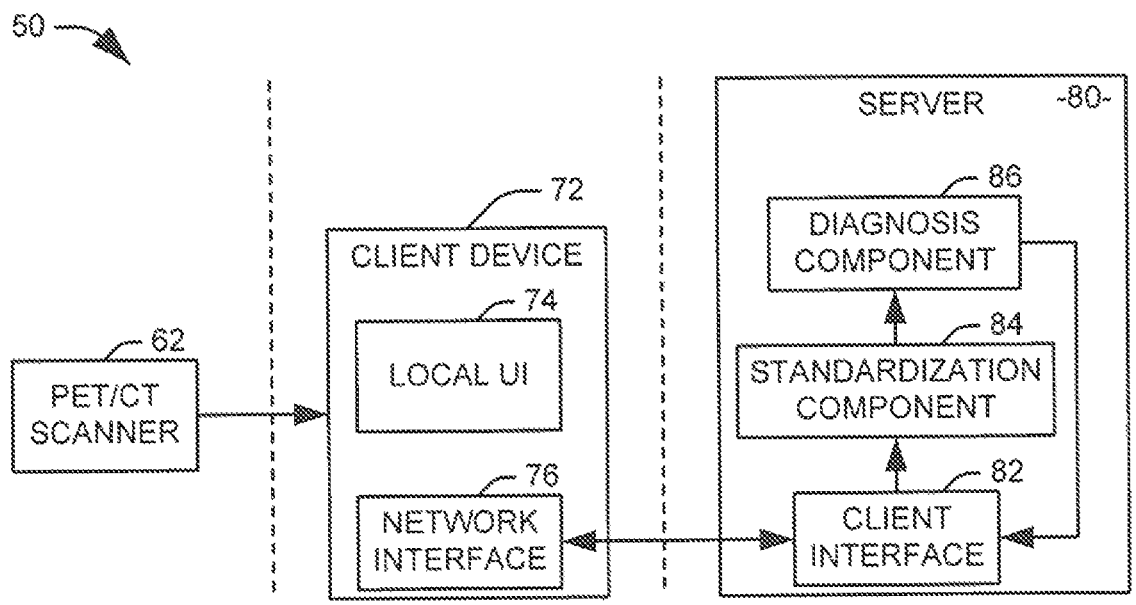
FIG. 2 illustrates a system for identifying diseased tissue within a PET scan in accordance with an aspect of the present invention.

FIG. 2 illustrates a system 50 for identifying diseased tissue within a PET scan in accordance with an aspect of the present invention. It will be appreciated that PET scans are often taken in a clinical location and provided electronically to another location, in which an expert user, such as a physician, technician, or similar individual, can review the results and, if needed, report any abnormalities back to a clinician. Accordingly, in the illustrated implementation, the system 50 can be distributed over multiple locations, including a first location associated with a clinical setting, a second location associated with a user, and a server 80, which can be a physical or virtual server. It will be appreciated that the server 80 can be located at the first location, the second location, a third location (not shown) or distributed across multiple computer systems in different locations.

The illustrated system 50 includes, at the first location, a positron emission tomography/computed tomography (PET-CT) scanner 62 configured to generate a PET-CT scan, providing glucose utilization data registered to anatomical data. This data can be transmitted to a client device 72 at the second location. In the illustrated implementation, the client device 72 is a stand-alone computer with a local user interface (UI) program 74 for receiving data from the user, although it will be appreciated that the client could be a workstation operating interface software as a service at the server 80. The local user interface 74 prompts the user to provide a first set of one or more intensity values, representing regions of interest within the PET scan, as well as a second set of intensity values taken from healthy regions of the hepatic parenchyma. In the illustrated implementation, the second set of intensity values has three values taken from different locations within the hepatic parenchyma, as it has been determined that glucose uptake within the liver is substantially stable from fifty minutes after injection one hundred ten minutes after injection. Once the values have been entered, they are provided to the server via a network interface 76.

The server 80 can be any physical or virtual server comprising machine executable instructions stored on one or multiple non-transitory computer readable media and executed by one or more associated processors. The server 80 includes a client interface 82 configured to receive the first set of intensity values representing the region of interest and the second set of intensity values representing the liver from the client device 72. A standardization component 84 is configured to calculate a correction value as a function of the second set of intensity values and apply the correction value to a chosen one of a decision threshold associated with the region of interest and the first set of intensity values. In the illustrated implementation, the correction value is calculated by taking an arithmetic mean of the second set of intensity values and calculating a ratio of an average value for a population of patients, such as a mean or median, to the calculated mean. Each of the first set of intensity values is then multiplied by the correction value to provide values corrected for the unique glucose utilization of the patient.

In an alternate embodiment, the correction value can instead be applied to the decision thresholds to which the first set of intensity values will be compared. In this instance, the correction value is instead calculated by taking an arithmetic mean of the second set of intensity values and calculating a ratio of an average value for a population of patients, such as a mean or median, to the calculated mean and multiplying all thresholds by the correction value. It will be appreciated that this approach can be used most easily in an initial identification of diseases tissue, whereas adjusting the intensity values directly can be used in comparing results across time, for example, in determining a response to treatment of the diseased tissue.

A diagnosis component 86 is configured to compare the first set of intensity values to the decision threshold associated with the region of interest to determine if the glucose uptake within the region of interest is abnormal. The decision threshold can be a determined threshold value over a population of patients for a given type of tissue, and that each type of tissue may have multiple decision thresholds. For example, values of 4.0 or greater would indicate malignancy for mediastinum, with values less than or equal to 3.1 indicating non-malignant tissue, and values between 3.1 and 4.0 indicating a borderline classification. For soft tissue lymph nodes, values of 2.5 or greater could indicate malignancy, with values less than or equal to 2.05 indicating non-malignant tissue, and values between 2.05 and 2.5 indicating a borderline classification. In the illustrated examples, more complex decision criteria can be used in accordance with the standardization principles taught herein. For example, for hepatic parenchymal tissue, a finding of malignancy can be made if the corrected value is equal to or greater than 4.0 and the ratio of the corrected value in the region of interest is at least twice that of the corrected value in identified normal tissue, normal classification if the corrected value is less than or equal to 3.15 and the ratio of the corrected value to the corrected value of the normal liver tissue is less than or equal to 1.64, and otherwise considered borderline.

Further, it will be appreciated that the decision, threshold can be based on previous measurements of a same patient, for example, to track disease progression or treatment efficacy. In this implementation, the decision threshold can be computed as a function of previous corrected intensity value from the region of interest. For example, each of the European Organization for Research and Treatment of Cancer (EORTC) criteria and the PET Response Criteria in Solid Tumors (PERCIST) criteria each utilize a decision threshold calculated as a percentage deviation from a previously measured value, and these criteria can be adapted to use the corrected intensity values of the illustrated system. It should be noted that the correction value utilized in the illustrated system is drawn from a PET of the liver taken contemporaneously with the measured intensity values, and thus corrects not only for variation among patients but for variation in the glucose usage of a given patient across time and for the differences in different imaging platforms. Once a determination is made, the client interface 82 provides the determination if the glucose uptake within the region of interest is abnormal to the client device 72 for review by the user.

Figure 3:
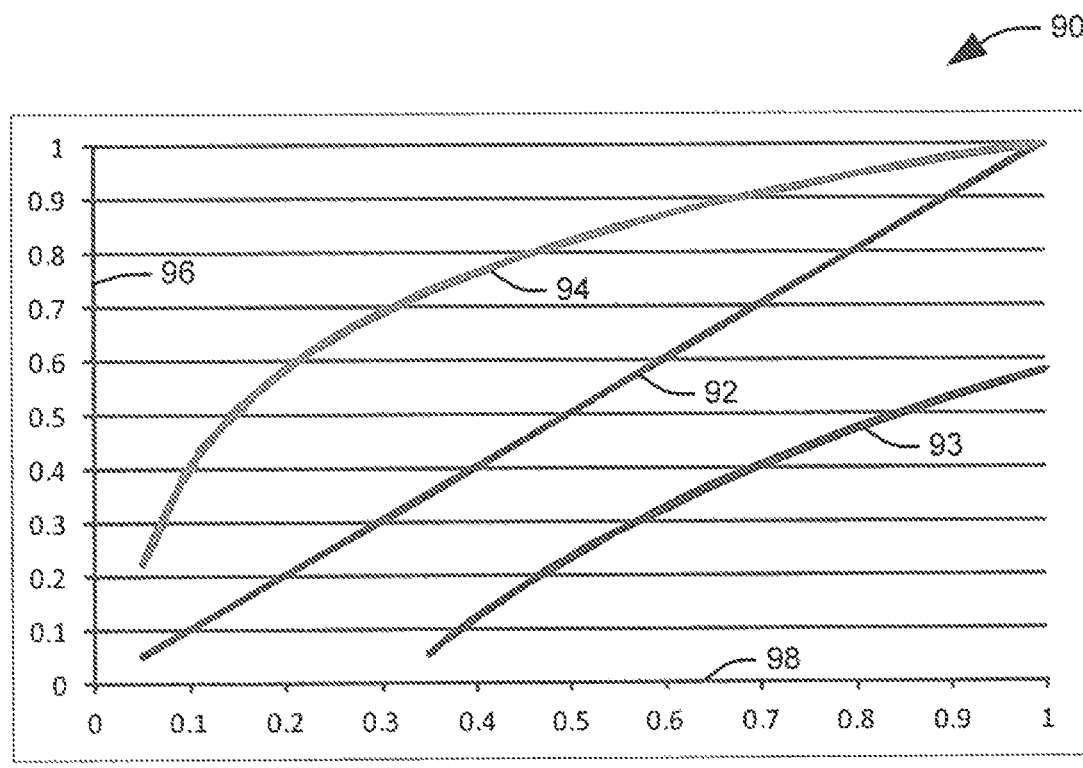
FIG. 3 is a graph illustrating Receiver-Operator-Characteristic (ROC) curves tor three methods of identifying of primary lung carcinoma in the thoracic pleura.

FIG. 3 is a graph 90 illustrating Receiver-Operator-Characteristic (ROC) curves 92-94 for three methods of identifying of primary lung carcinoma in the thoracic pleura. In the illustrated implementation, corrected intensity values greater than or equal to 3.0 indicate carcinoma. A vertical axis 96 represents sensitivity, that is, the rate of accurate positive results, and a horizontal axis 98 represents a false positive rate, effectively the difference between 1 and a specificity of the method. The three ROC curves 92-94 include a first ROC curve 92 representing a random guess methodology and referred to herein as the "no-discrimination line", a second ROC curve 93 representing the use of uncorrected SUVs with the decision threshold given above, and a third ROC curve 94 representing the use of intensity values, corrected as discussed previously with respect to FIGS. 1 and 2, with the decision threshold given above. It will be appreciated that the second ROC curve 93 is completely below the no-discrimination line, and thus is consistently worse than chance, with the area under the second ROC curve being 0.0912. In contrast the third ROC curve 94, using the corrected intensity values, is significantly better than chance, with an area under the curve of 0.7458.

Accordingly, a significant increase in the accuracy of the classification can be achieved.

Figure 4:
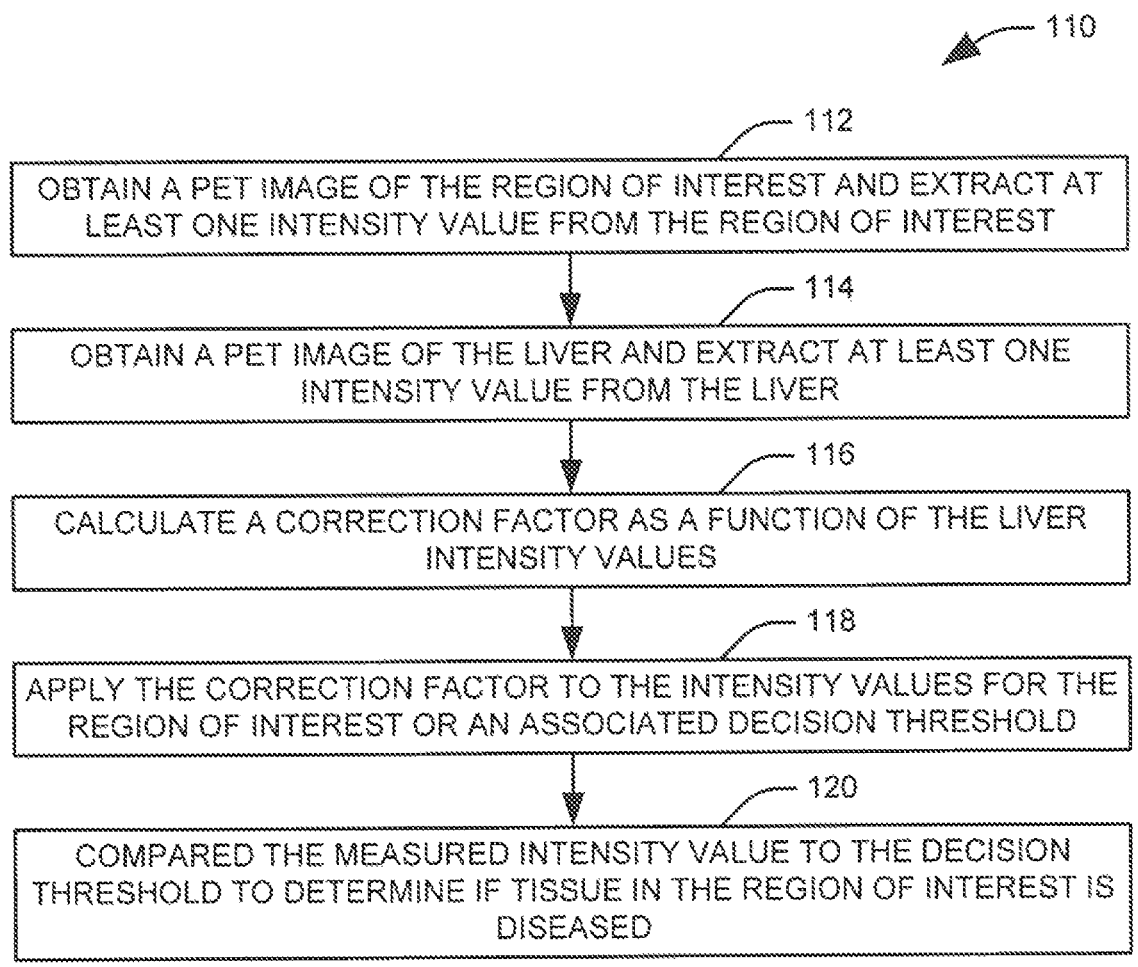
FIG. 4 illustrates a method for distinguishing diseased tissue from healthy tissue within a region of interest of a patient in accordance with an aspect of the present invention.

In view of the foregoing structural and functional features described above, a method in accordance with various aspects of the present invention will be better appreciated with reference to FIG. 4. While, for purposes of simplicity of explanation, the method of FIG. 4 is shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement a method in accordance with an aspect the present invention.

FIG. 4 illustrates a method 110 for distinguishing diseased tissue from healthy tissue within a region of interest of a patient in accordance with an aspect of the present invention. At 112, one or more PET images are obtained of the region of interest and at least one measured intensity value is extracted from the region of interest. At 114, a PET image is obtained of the liver of the patient and at least one liver intensity value is extracted from a selected portion of the liver. For example, either a user or an automated system can locate one or more regions of healthy tissue within the liver, for example, within the hepatic parenchyma, from which the liver intensity values can be extracted. At 116, a correction factor can be calculated as a function of the at least one liver intensity value. In one implementation, the correction factor can represent a ratio of a representative value, such as an average value, determined from the at least one liver intensity value, and a population liver SUV representing an average or otherwise representative SUV for a population of patients. It will be appreciated that by the term "average," any measure of central tendency can be used, including, for example, the arithmetic mean, the geometric mean, the median, and mode. The population SUV can be drawn from the general population or a subset of the general population sharing one or more characteristics with the patient, such as age, sex, height, weight, or medical history.

At 118, the correction factor is applied to one or both of the set of at least one measured intensity value and a set of at least one decision threshold associated with the region of interest. Where multiple intensity values are measured to represent the region of interest, the correction factor can be applied to each of them prior to calculation of a representative value, such as an average (e.g., mean, median, or mode), or it can be applied to the representative value itself, depending on the nature of the representative value. It will be further appreciated that the rate of glucose absorption can be different for different types of tissues, and thus regions of interest from different portions of the patient's body can have different decision thresholds. Further, it will be appreciated that a given region of interest can have a single decision threshold, representing a binary "healthy" or "diseased" decision, or multiple decision thresholds, representing different probabilities that the tissue is diseased. Where multiple decision thresholds are used, the correction factor is applied to each of them. At 120, the measured set of intensity values is then compared to the one or more decision thresholds to determine if the tissue in the region of interest is diseased.

The inventor has found that the correction value can standardize PET readings across platforms and patients, allowing for meaningful comparison of PET results among themselves and clinically established thresholds. Accordingly, the accuracy of disease diagnosis and treatment monitoring can be significantly increased, with the associated decrease in costs and betterment of outcomes.

Figure 5:
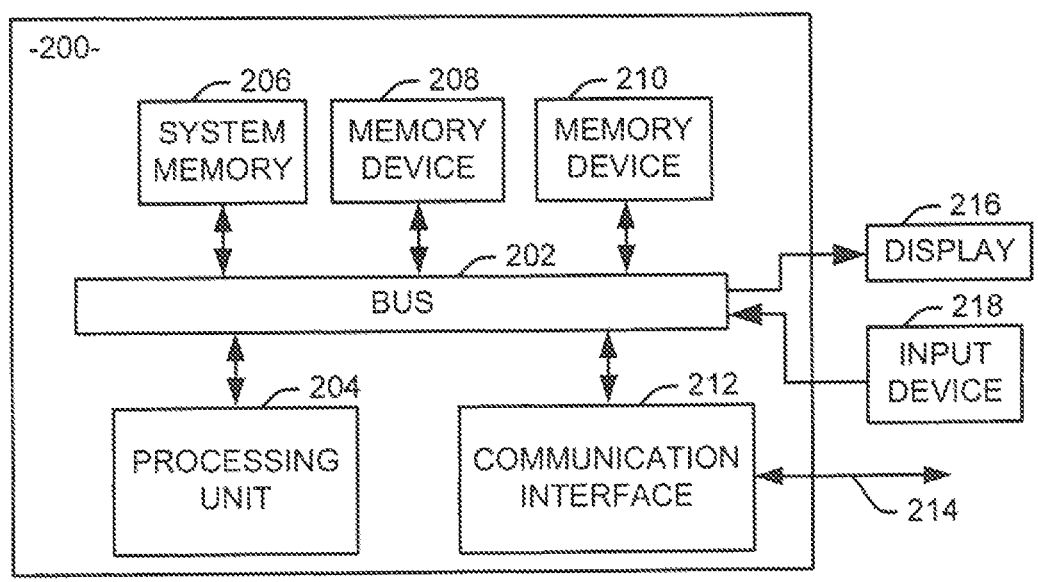
FIG. 5 is a schematic block diagram illustrating an exemplary system of hardware components capable of implementing examples of the systems and methods disclosed in FIGS. 1-4.

FIG. 5 is a schematic block diagram illustrating an exemplary system 200 of hardware components capable of implementing examples of the systems and methods disclosed in FIGS. 1-4. The system 200 can include various systems and subsystems. The system 200 can be a personal computer, a laptop computer, a workstation, a computer system, an appliance, an application-specific integrated circuit (ASIC), a server, a server blade center, a server farm, etc.

The system 200 can includes a system bus 202, a processing unit 204, a system memory 206, memory devices 208 and 210, a communication interface 212 (e.g., a network interface), a communication link 214, a display 216 (e.g., a video screen), and an input device 218 (e.g., a keyboard and/or a mouse). The system bus 202 can be in communication with the processing unit 204 and the system memory 206. The additional memory devices 208 and 210, such as a hard disk drive, server, stand-alone database, or other non-volatile memory, can also be in communication with the system bus 202. The system bus 202 interconnects the processing unit 204, the memory devices 206-210, the communication interface 212, the display 216, and the input device 218. In some examples, the system bus 202 also interconnects an additional port (not shown), such as a universal serial bus (USB) port.

The processing unit 204 can be a computing device and can include an application-specific integrated circuit (ASIC). The processing unit 204 executes a set of instructions to implement the operations of examples disclosed herein. The processing unit can include a processing core.

The additional memory devices 206, 208 and 210 can store data, programs, instructions, database queries in text or compiled form, and any other information that can be needed to operate a computer. The memories 206, 208 and 210 can be implemented as computer-readable media (integrated or removable) such as a memory card, disk drive, compact disk (CD), or server accessible over a network. In certain examples, the memories 206, 208 and 210 can comprise text, images, video, and/or audio, portions of which can be available in formats comprehensible to human beings.

Additionally or alternatively, the system 200 can access an external data source or query source through the communication interface 212, which can communicate with the system bus 202 and the communication link 214.

In operation, the system 200 can be used to implement one or more parts of a medical imaging and analysis system utilizing patient-specific correction for PET intensity values in accordance with the present invention. Computer executable logic for implementing the system control 126 resides on one or more of the system memory 206, and the memory devices 208, 210 in accordance with certain examples. The processing unit 204 executes one or more computer executable instructions originating from the system memory 206 and the memory devices 208 and 210. The term "computer readable medium" as used herein refers to a medium that participates in providing instructions to the processing unit 204 for execution, and can include either a single medium or multiple non-transitory media operatively connected to the processing unit 204.

The invention has been disclosed illustratively. Accordingly, the terminology employed throughout the disclosure should be read in an exemplary rather than a limiting manner. Although minor modifications of the invention will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

I claim:

1. A system for evaluating tissue for abnormal glucose uptake within a region of interest within a patient, the system comprising:

a positron emission tomography (PET) scanner configured to obtain a set of at least one PET image that includes a first set of at least one intensity value representing glucose uptake in the region of interest and a second set of at least one intensity value representing glucose uptake in a liver of the patient;

a standardization component configured to calculate a correction value as a function of a ratio of a value representing the second set of at least one intensity value to an average liver standard uptake value (SUV) for a population of patients and apply the correction value to each of the first set of at least one intensity value representing glucose uptake in the region of interest to provide a corrected set of at least one intensity value; and a display configured to display the corrected set of at least one intensity value to a user.

2. The system of claim 1, wherein the standardization component calculates the value representing the second set of at least one intensity value by selecting an intensity value for each of a plurality of regions within the liver and calculating a mean value for the selected intensity values across the plurality of regions.

3. The system of claim 1, wherein the PET scanner is a positron emission tomography/computed tomography (PET-CT) scanner configured to provide PET and CT data for the region of interest and the liver.

4. A method for evaluating tissue within a region of interest within a patient, the method comprising:

administering radiolabeled 18F deoxyglucose (FDG) to the patient;

performing a positron emission tomography (PET) scan at an associated PET scanner to provide an intensity value representing glucose uptake in the region of interest and a second set of at least one intensity value representing glucose uptake in a liver of the patient;

calculating a correction value as a function of a ratio of a value representing the second set of at least one intensity value to an average standard uptake value (SUV) for liver tissue across a population of interest; and applying the correction value to the intensity value representing glucose uptake in the region of interest to provide a corrected intensity value.

5. The method of claim 4, further comprising comparing the corrected intensity value to a decision threshold determined as a function of a third set of at least one intensity value for the patient.

6. The method of claim 4, wherein calculating the value representing the second set of at least one intensity value comprises:

selecting a plurality of regions within the hepatic parenchyma within the PET scan;

determining an intensity value for each of the plurality of regions; and calculating a mean value for the determined intensity values across the plurality of regions to provide the value representing the second set of at least one intensity value.

7. The method of claim 4, wherein the intensity value representing glucose uptake in the region of interest is a first value of a plurality of values representing glucose uptake in the region of interest and the method further comprises:

determining an average value of the plurality of values representing glucose uptake in the region of interest; and comparing the average value to a decision threshold.

8. The method of claim 7, wherein applying the correction value to the intensity value representing glucose uptake in the region of interest comprises applying the correction value to the average value.

9. The method of claim 7, wherein applying the correction value to the intensity value representing glucose uptake in the region of interest comprises applying the correction value to each of the plurality of values representing glucose uptake in the region of interest before determining the average value of the plurality of values representing glucose uptake in the region of interest.

* * * * *